United States Patent [19]

Schmitt et al.

[11] Patent Number: 4,972,092

[45] Date of Patent: Nov. 20, 1990

[54] APPARATUS FOR DETERMINING THE EFFECTIVE SURFACE ROUGHNESS OF POLISHED OPTICAL SAMPLES BY MEASURING THE INTEGRAL SCATTERED RADIATION

[75] Inventors: Dirk-Roger Schmitt, Braunschweig; Helmut T. A. Rosteck, Wolfenbüttel, both of Fed. Rep. of Germany

[73] Assignee: Deutsche Forschungsanstalt fur Luftund Raumfahrt, Cologne, Fed. Rep. of Germany

[21] Appl. No.: 408,532

[22] Filed: Sep. 15, 1989

[30] Foreign Application Priority Data

Sep. 20, 1988 [DE] Fed. Rep. of Germany .... 3831907.1

[51] Int. Cl.$^5$ ............................................. G01N 21/47
[52] U.S. Cl. .................................. 250/571; 250/228; 356/236
[58] Field of Search ................ 250/228, 571; 356/236, 356/445, 446, 447

[56] References Cited

U.S. PATENT DOCUMENTS 3,874,799  4/1975  Isaacs et al. ...................... 356/236

4,703,187  10/1987  Höfling et al. ...................... 250/228

OTHER PUBLICATIONS

Optik, 65 No. 2 (1983), pp. 143–151.
Applied Optics, vol. 23, No. 21, Nov. 1, 1984, pp. 3820–3825.
American Society for Testing Materials, ASTM Designation: F1048-87, Standard Test Method for Measuring the Effective Surface Roughness of Optic Components by Total Integrated Scattering.

*Primary Examiner*—David C. Nelms
*Assistant Examiner*—George C. Beck
*Attorney, Agent, or Firm*—Salter & Michaelson

[57] ABSTRACT

Apparatus for determining the effective surface roughness of polished optical samples, by measuring the total integrated scattering, only operates for non-light-transmissive samples. For a transmissive sample, the invention adds a light trap behind the sample for transmitted light, and a diaphragm in front of the sample. The rear surface of the diaphragm is provided with a non-reflective wafing which traps secondary light reflected or scattered by the inside rear surface of the sample.

12 Claims, 6 Drawing Sheets

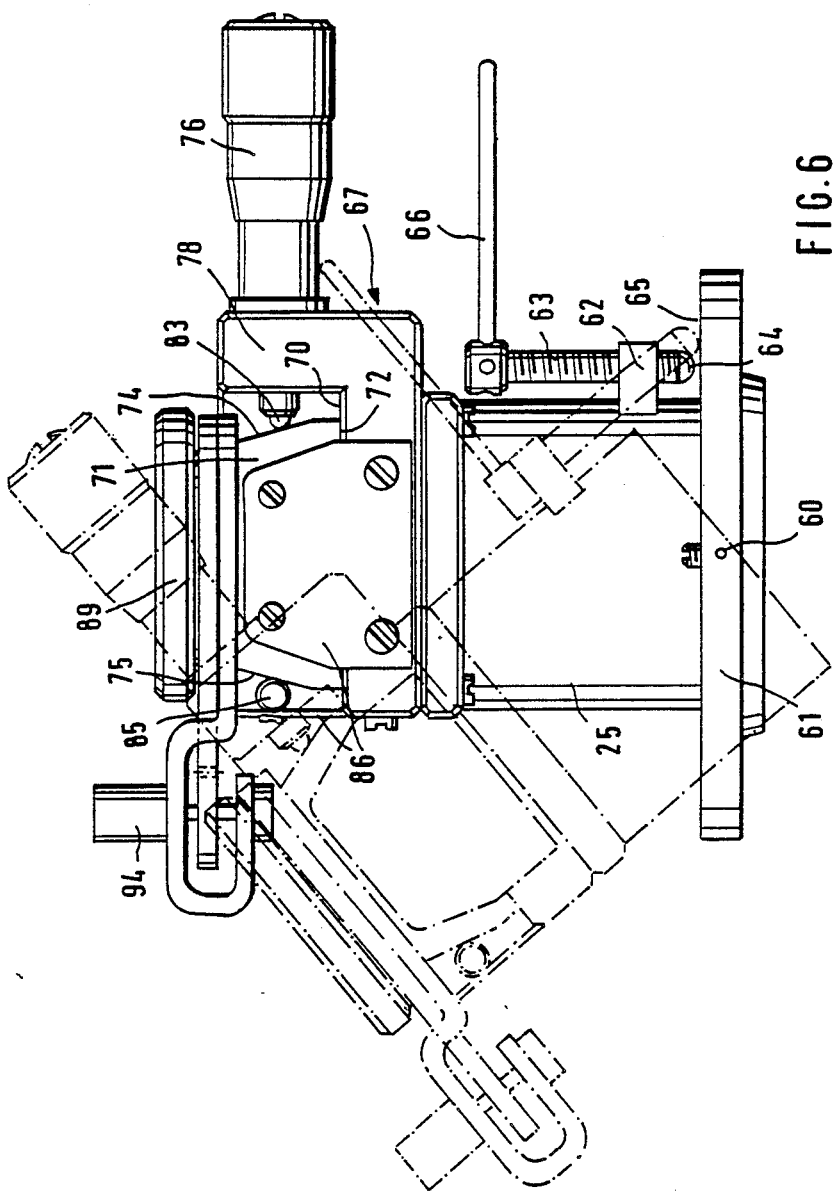

APPARATUS FOR DETERMINING THE EFFECTIVE SURFACE ROUGHNESS OF POLISHED OPTICAL SAMPLES BY MEASURING THE INTEGRAL SCATTERED RADIATION

The invention relates to an apparatus for determing the effective surface roughness of polished optical samples by measuring the integral scattered radiation (total integrated scattering).

BACKGROUND OF THE INVENTION

In order to measure the integral scattered liminous radiation, on the one hand apparatus is known which works with an Ulbricht sphere (see Optik, 65 No. 2 (1983), pages 143–151; A plied Optics, Vol. 23, No. 21/1, November 1984, pages 3820–3825). Other apparatus is known which works with a Coblentz hemisphere (American Society for Testing Materials, ASTM designation: F, 1048-87, Standard Test Method for Measuring the Effective Surface Roughness of Optic Components by Total Integrated Scattering).

In the known methods, the sample to be examind is illuminated with a laser beam of a specific wavelength, and the light scattered by the surface of the sample is determined integrally with the Ulbricht sphere or the Coblentz hemisphere and is accepted as a measure for evaluating the surface quality of the sample.

The Ulbricht sphere is a hollow sphere which is coated on its inside with a material which scatters ideally and which is provided with a first opening for the entry of the beam of light and a second opening for the exit of the beam reflected from the surface of the sample and with a support for holding the sample in the region of the sphere wall, and it comprises a detector, disposed in the sphere wall, for the integral scattered light.

The Coblentz hemisphere is a complete or approximately complete hemisphere which is mirror-coated on its inside and is provided with a first opening for the entry of the beam of light and a second opening for the exit of the beam reflected from the sample, wherein the point of incidence of the light on the sample is offset laterally in relation to the axis of the hemisphere and the detector is disposed in the focal point of the scattered light of the sample reflected from the mirror-coated surface.

Apparatuses of the kind in question only permit examination of the surface of samples which do not have any light transmission, that is to say only of samples which are strongly reflecting or strongly absorbing.

In the case of transparent samples, the beam of light also falls on the back of the sample. There scattered light is likewise produced which is reflected from the back of the sample. This scattered light reflected from the back of the sample is superimposed on the scattered light which is reflected from the front of the sample. Thus no quantitative measurement or determination of the scattered light originating from the polished front of the sample is possible.

SUMMARY OF THE INVENTION

The subject of the invention is an apparatus for determining the effective surface roughness of transparent optical samples, the surface of which is polished, by measuring the total scattered radiation having an adjustable support for the sample, a source of laser light from which a beam of light is directed onto the surface of the sample at an angle between 15° and 45°, a light trap for the beam of light reflected from the surface of the sample, an apparatus for measuring the scattered light reflected from the surface of the sample with a light detector and a display device for the measured scattered light, an opening in the sample support for the beam emerging at the back of the transparent sample in the direction of the incident beam, a light trap disposed behind this opening for this beam component, and a masking diaphragm disposed on the sample support for the sample with an opening for the incident beam and the beam reflected from the surface of the sample, which diaphragm is made light-absorbing at least in the region of the beam component reflected directly from the back of the transparent sample.

In such an apparatus, even with a transparent sample, the integral scattered light which originates from the polished surface on which the incident beam of light falls is measured exclusively.

In one form of embodiment of such an apparatus, an Ulbricht sphere is used which integrates the scattered light and which is coated on its inside with a material which scatters ideally and is provided with a first aperture for the entry of the beam of light and a second aperture for the emergence of the beam reflected from the surface of the sample and with an adjustable support to hold the sample in the region of the sphere wall, and which comprises a detector disposed in the sphere wall for the integral scattered light.

In a further form of embodiment, a Coblentz hemisphere is used which is mirror-coated on its inside and is provided with a first aperture for the entry of the beam of light and a second aperture for the emergence of the beam reflected from the sample, wherein the point of incidence of the light on the sample is offset laterally in relation to the axis of the hemisphere and the detector is disposed in the focal point of the scattered light of the sample reflected from the mirror-coated surface.

In a first form of embodiment, the masking diaphragm can be provided, in the region of the beam reflected from the back of the sample, with an aperture which is covered by a light trap. In this case, a polished silicon disc which is coated with at least one dielectric $\lambda/4$ layer at least on the surface adjacent to the aperture, may be provided as a light trap.

The whole masking diaphragm may, however, also be coated with at least one dielectric $\lambda/4$ layer at least on the surface adjacent to the sample surface. The $\lambda/4$ coating in this case preferably consists of a dielectric material with a refractive index $n \approx 2$, and $Ta_2O_5$, $TiO_2$, $ZrO_2$ or $Al_2O_3$ is preferably provided as a coating.

In one form of embodiment, the sample support is mounted by an outer housing in a flange which surrounds the aperture for the beam emerging at the rear of the sample, and an inner housing with a sample holding means is mounted in the outer housing and is adapted for adjustment in two directions at right-angles to the axis of the sample holding means and at right-angles to one another, and the inner housing and the outer housing are provided with light-transmitting apertures in the direction of the beam passing through the sample.

The outer housing may appropriately be pivotable, in the flange, about an axis which passes through the point at which the incident beam strikes the surface of the sample and which extends perpendicularly through the apex of the angle between the incident and emergent beam.

One of the adjustment directions of the inner housing relative to the outer housing extends perpendicular to the pivot axis while the other adjustment direction extends in the direction of the pivot axis.

The sample holder is preferably mounted in the inner housing for rotation about its axis, while a plurality of beam-transmitting apertures are provided in its wall.

In an appropriate form of embodiment, the sample holder can be inserted in an intermediate sleeve which is rotatably mounted in the inner housing and is provided with a rotary drive, the intermediate sleeve being provided with the same beam-transmitting apertures as the sample holder.

BRIEF DESCRIPTION OF THE DRAWINGS

The invention is illustrated with examples of embodiment in the drawing and described in detail below with reference to the drawing.

FIG. 6 shows a side view with a tilted position illustrated in broken lines.

DESCRIPTION OF THE PREFERRED EMBODIMENTS

Figure 1:
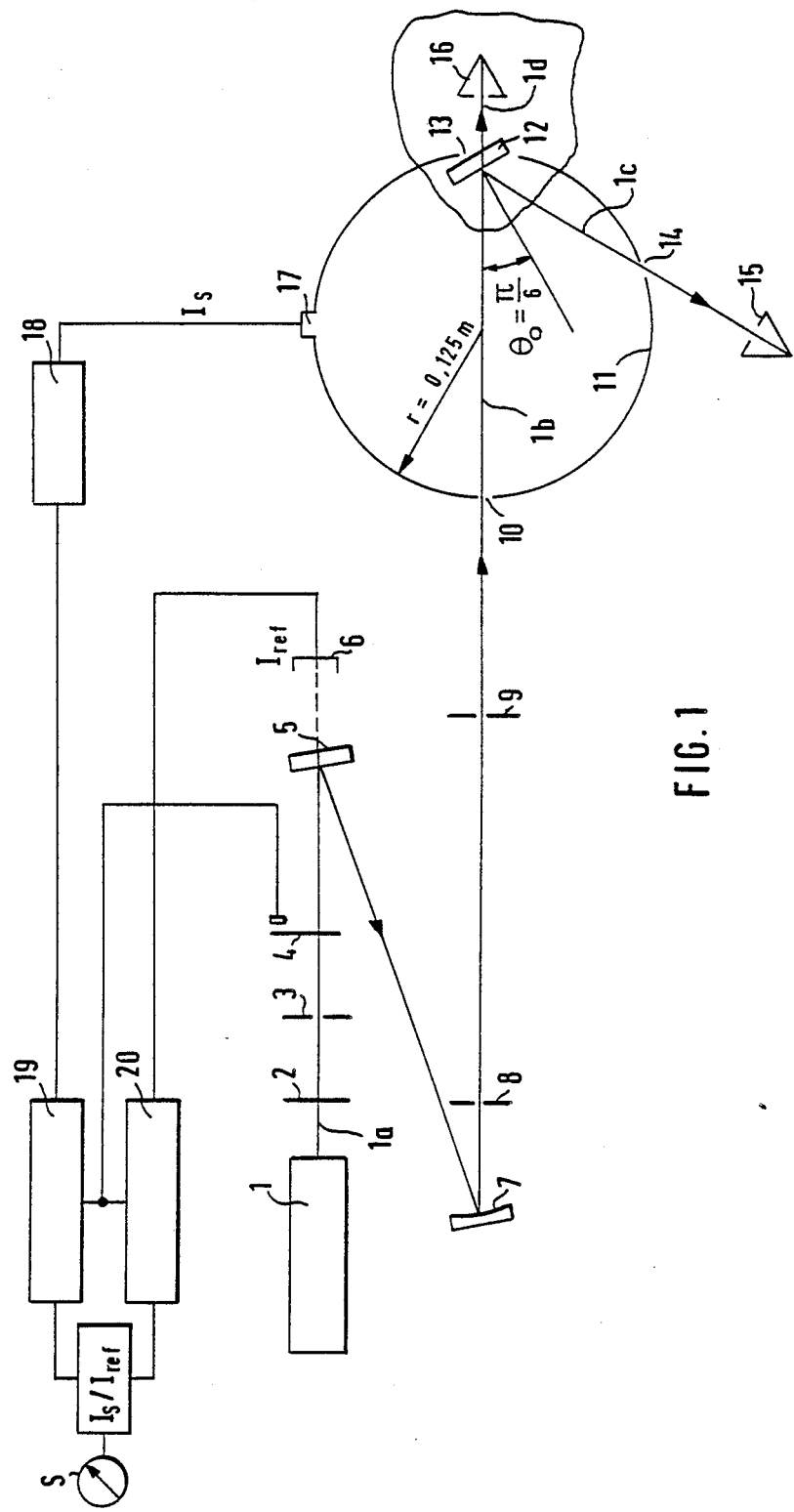
FIG. 1 shows the diagrammatic construction of an apparatus for measuring the integral scattered light by means of an Ulbricht sphere.

In FIG. 1, the principle of the construction and mode of operation of an apparatus for measuring the integral scattered light by means of an Ulbricht sphere is illustrated. A laser 1, for example an HeNe laser (the wavelength depends on the measuring task), is provided as a light source. According to the problem posed, the beam of light 1a originating from the laser is polarized by a polarizer 2, falls through a diaphragm 3 and is converted into chopped light at a chopper 4. The chopped light impinges on a mirror 5 from which the predominant part of the light is reflected. Some of the light penetrates through the mirror 5, falls on a photodetector 6 which delivers a reference signal $I_{ref}$. The reflected light is reflected again on a mirror 7. The mirror 7 is a concave mirror with a radius of 2 m. After that, the beam of light passes through two further diaphragms 8, 9. Then it passes through an inlet aperture 10 into an Ulbricht sphere 11.

The Ulbricht sphere is a hollow sphere with a radius of 0.125 m. Inside, the sphere is coated with a material which is almost ideally scattering, for example $B_aSO_4$. The beam of light falls at an angle $\theta_O=\pi/6$ on the sample 12 which is mounted on a sample support in a sphere aperture 13 diametrically opposite the inlet aperture 10. The sample consists of a transparent optical glass which is polished to optical quality at least on its surface facing the incident beam of light, hereinafter called the "front". The light reflected on the front of the sample 12 emerges from the sphere through an aperture 14, which is situated at an angle of $2\theta_O=\pi/3$ to the incoming beam and falls into a light trap 15. The light penetrating through the sample 12 reaches the outside through the aperture 13 and falls into a light trap 16. The angle $\theta$ can be selected between 15° and 45°. It is preferably about 30°.

The light scattered in the whole cavity of the sphere 11 is integrated by the Ulbricht sphere and measured by the detector 17. The signal $I_s$ passes through apreamplifier 18 to a lock-in amplifier 19 for amplification. The reference signal $I_{ref}$ is processed in the lock-in amplifier 20. both amplifiers receive the reference frequency from chopper 4. Then the quotient $I_s/I_{ref}$ is formed which gives a measure for the scattered light S and is used to judge the effective surface roughness of the polished front.

Figure 2:
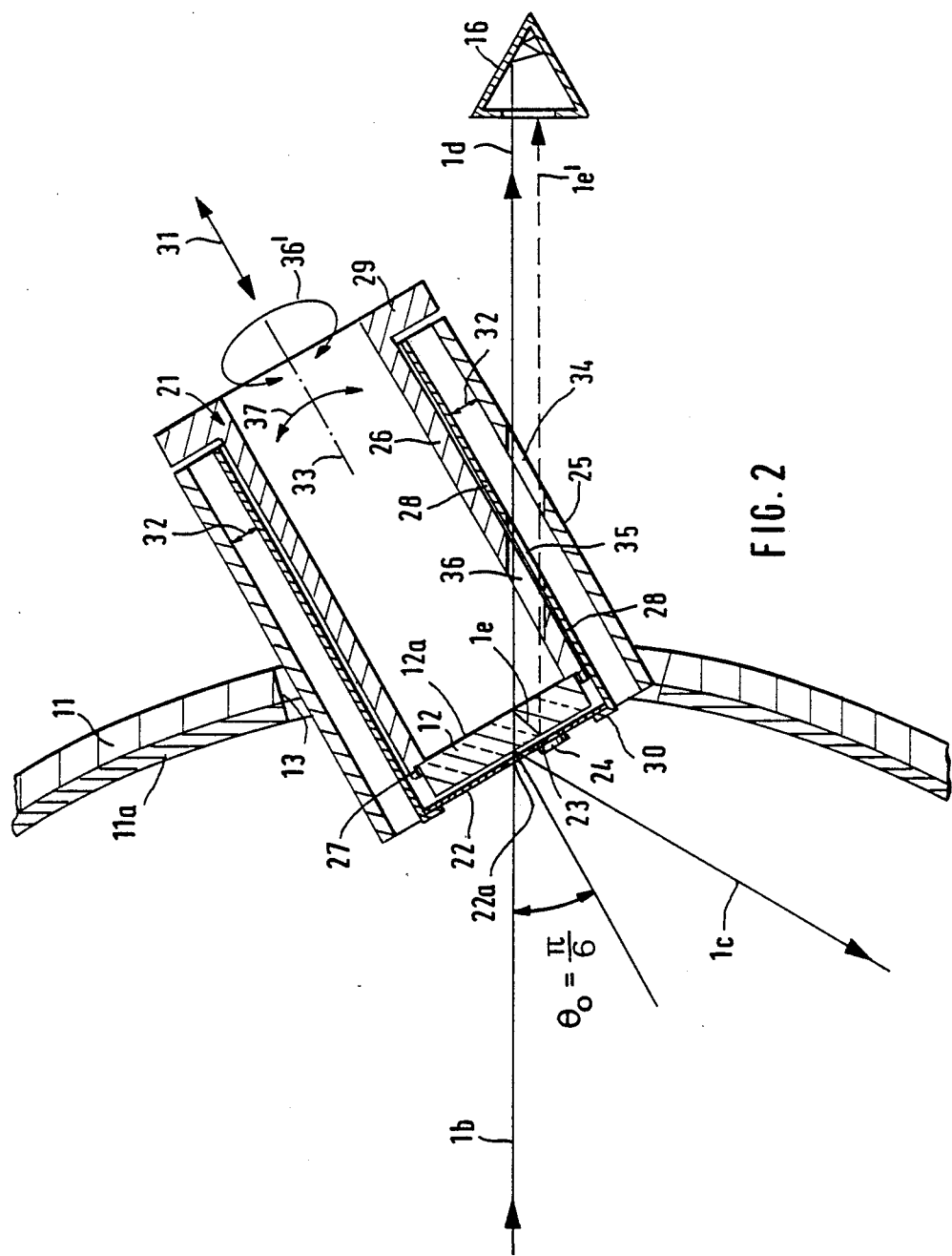
FIG. 2 shown the detail of the Ulbricht sphere outlined in FIG. 1, with the sample support.

The course of the beam of light at the sample and the sample support is reproduced on a larger scale in FIG. 2. The inside wall of the sphere 11 is provided with an ideally scattering coating 11a, preferably with a coating of $BaSO_4$. The sample 12, consisting of a light-transmissive material, is mounted in the spere opening 13 by means of a holding device 21 and is covered by a diaphragm 22 which is provided, in the middle, with an aperture 22a through which the dincident beam 1b impinges on the sample and the beam 1c reflected from the sample surface emerges. The diaphragm 22 prevents scattered light reflected from the back 23 of the sample from getting back into the Ulbricht sphere. Thus the scattered light originating from the front of the sample is measured exclusively. The diaphragm 22 consists of a thin, round disc, the surface of which is adapted to absorb the laser light and may be blackened for example. A round transmission aperture 22a made with a sharp edge is provided in the middle of the diaphragm and may have a diameter of about 1 mm. The outside diameter of the diaphragm is so large that the sample to be measured, which may have a diameter of about 25 mm for example, is completely covered.

In the case of a light-transmissive sample, the light, as already described above, is partially reflected on the front of the sample and leaves the sphere through the aperture 14. The light scattered on the front of the sample passes completely into the sphere and can be measured. The light falling from the front into the sample impinges on the back 23 of the sample and is again transmitted with a beam component 1d. Some of the light falling into the sample is, however, also reflected from the back of the sample—beam component 1e—and then reflected again on the front of the sample—beam component 1e'. In the course of this, scattered radiation is also produced.

In all scattering processes, most of the light is scattered in the direction of the reflected beam. Now the diaphragm 22 is so constructed that the beam component 1e reflected from the back of the sample and the scattered light from the back of the sample are prevented from being able to enter the sphere.

For this purpose, the diaphragm 22 is so designed and the angle of incidence of the light is so selected that the light reflected at the back of the sample is caught by the diaphragm. In order to avoid light scattering again occurring at the point where the reflected beam component 1e impinges on the diaphragm, a light trap is provided for the beam component 1e.

In the embodiment shown in FIG. 2, a further aperture 23 is provided in the diaphragm, in the region of the point where the reflected beam component 1e impinges, for this light beam 1e reflected from the back of the sample. A light trap is mounted behind this aperture in the direction of the beam, that is to say at the front of the diaphragm. This light trap may, for example be a silicon disc 24 0.3 mm thick, of which the surface facing the aperture 23 is polished and dereflected by a coating of a dielectric material. This material preferably has a refractive index n of about 2.0 such as is found, for example in $Ta_2O_5$, $TiO_2$, $ZrO_2$ or $Al_2O_3$. The layer thickness d must then be fixed so that $n.d = \lambda/4$ at which the wavelength of the laser light used is. Since the polished silicon disc has a refractive index of $n = 4.05$ in the visible spectral range, without dereflection, it has a reflection of about 0.30. This reflection is reduced to 0.003 by the coating. Since silicon has an absorption index $k = 0.5$, the effect is achieved by the coating that nearly all the incident light is absorbed in this light trap. Thus the silicon disc 24 mounted on the diaphragm 22 as a light trap ensures that nearly all the light reflected and scattered at the back of the sample 23 is absorbed. No light scattering is produced at the coated silicon disc 24.

The diaphragm 22 may also the made completely from a thin silicon disc polished on both sides. In this case, both its front and its back may appropriately be coated. Thus the whole diaphragm becomes a light trap. The additional aperture 23 is the diaphragm and the silicon disc 24 as a light trap are then no longer necessary. The coating on the front of the diaphragm of silicon leads to the fact that light which does not belong to the direct beam of light, such as scattered light from the deflecting mirrors of the apparatus or light diffracted at the entry aperture 10, is absorbed at the front of the diaphragm 22 and so can no longer falsify the measurement.

The holding device 21 represented diagrammatically in FIG. 2 comprises an outer housing 25 which is mounted in a flange which covers the opening 13 in the sphere and is not illustrated in FIG. 2. The sample 12 is secured to a tubular sample holder 26 and is gripped for example in a recess 27 in its one end. In this case, the sample rests against a shoulder formed by the recess. The sample holder 26 can be pushed, with a slight clearance, into an inner housing 28 and is provided with a flange 29 for handling the sample holder, at the opposite end to the sample. The inner housing is provided, at its end adjacent to the sample, with an inside flange 30 to which the diaphragm 22 is here secured and so follows the movements of the inner housing relative to the outer housing. The diaphragm 22 may, however, also be secured stationary at the lower end of the outer housing 25. The inner housing, with the sample holder 26 present therein is axially displaceable in the outer housing 25, as indicated by the double arrow 31.

The inner housing 28 is further adjustable two-dimensionally transversely in the outer housing, as indicated by the double arrow 32 and will be described below with reference to FIGS. 4 to 6.

The outer housing 25 can further be tilted in the covering flange, about an axis not illustrated in FIG. 2, which axis is perpendicular to the plane of the drawing and passes substantially through the point at which the beam of light 1b impinges on the sample 12—double arrow 37. The sample holder 26 is preferably mounted for rotation about its axis 33 with the inner housing 28—double arrow 36'.

In the direction of the incident beam 1b, the outer housing 25, the inner housing 28 and the sample holder 26 are provided with apertures 34, 35, 36 through which the beam component 1d, which has penetrated through the sample, falls. Furthermore, the beam component 1e' emerges here. The beam components 1d and 1e' are then caught in the light trap 16. If the sample is rotatable with the sample holder 26 in the inner housing 28, about the axis 33, as indicated by the double arrow 36', a number of light-transmitting apertures 35, 36 corresponding to the number of rotational positions provided must be provided in the sample holder 26.

The sample 12 is adjusted to the path of rays of the incident beam 1b by the various possibilities of adjustment corresponding to the double arrows 31, 32, 36', 37. The angle of incidence $\theta_O$ is set by the pivotal movement of the outer housing 25 in the mounting flange not illustrated. The point of incidence is adjusted and the various measuring points for a series measurement are set by the axial adjustment in the direction of the double arrow 3 and the two-dimensional displacement of the inner housing in the outer housing. As a result of the rotatability, it is possible to measure the scattered light component with different directions of incidence of the beam incident on the sample.

As a result of the fact that the laser light falls on the sample at a large angle (for example 30°), and as a result of the arrangement of an absorbing light trap at the diaphragm or the construction of the diaphragm as a light trap, the effect is achieved that no stray light from the back of the sample falls into the Ulbricht sphere. This light is successfully cut out or absorbed completely. As a result the scattered light from the front of the sample is measured exclusively. It is thus possible to measure the total integral scattered light of polished surfaces of transparent glass samples and to draw conclusions therefrom about the surface quality or the quality of their polishing.

Figure 3:
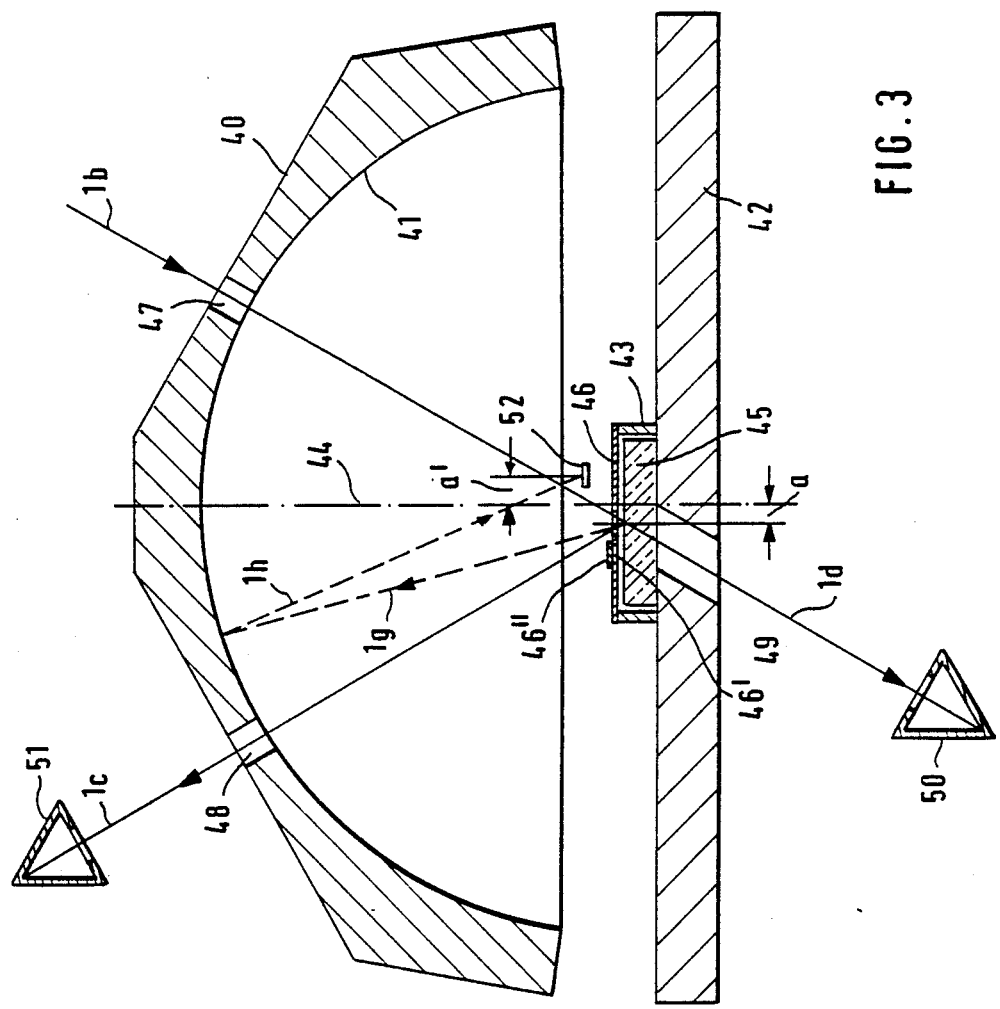
FIG. 3 shows diagrammaticaly, in section, a Coblentz hemisphere constructed according to the invention.

In FIG. 3, a Coblentz hemisphere is illustrated diagrammatically as a further apparatus for measuring the integral scattered radiation. This Coblentz hemisphere comprises a body 40 which is constructed at its inside 42 in the form of a complete or almost complete hemisphere. The spherical surface 41 is mirror-coated in order to achieve as high a reflectivity as possible. The body 40, constructed in the form of a hemisphere at its inside, lies over a supporting plate 42 on which there is disposed a sample holding means 43, in such a manner that it is adjustable at least two dimensionally transversely to the axis 44 of the hemispherical surface 41. The sample 45 is covered at its top by a diaphragm 46 which can be constructed in the same manner as described above with reference to FIG. 2.

An aperture 47 for the incident beam 1b and a second aperture 48 for the beam 1c reflected from the front of the sample are provided in the body 40. The two beams 1b and 1c form the angle $2\theta$ between them. In the extension of the incident beam 1b, an aperture 49 is provided in the supporting plate 42 for the beam 1d passing through the sample 45, in the optical path of which beam there is disposed a light trap 50. A further light trap 51 lies in the optical path of the beam 1c.

The point at which the incident beam 1b impinges on the front of the sample is offset laterally by the amount a in relation to the axis 44 of the hemisphere. A photodetector 52 is disposed in the focal point of the scattered light originating from the front of the sample, with substantially the same offsetting a' in relation to the axis 44 of the hemisphere. This scattered light is represented by way of example by an emerging scattered light component 1g and a reflected scattered light component 1h. With the arrangement described, all the scattered light which is reflected from the spherical surface 41 is focussed on the photodetector 52 so that this photodetector delivers a measured value which corresponds to the integral scattered luminous radiation. Otherwise, the apparatus with the Coblentz hemisphere is constructed in accordance with the apparatus shown in FIG. 1.

Figure 4:
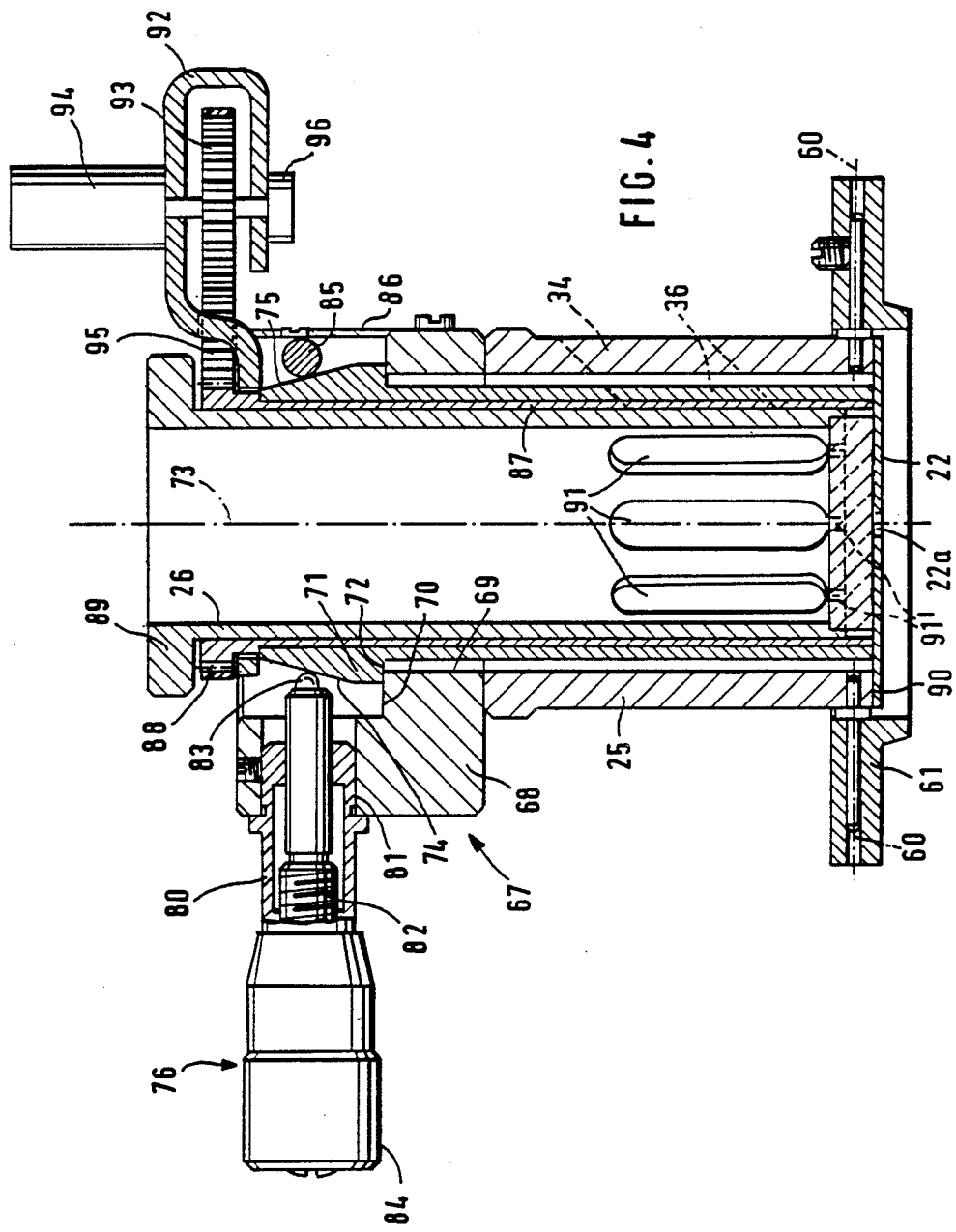
FIG. 4 shows a section through an adjustable holding means for the sample, which can be used in connection with an Ulbricht sphere or a Coblentz hemisphere.
Figure 5:
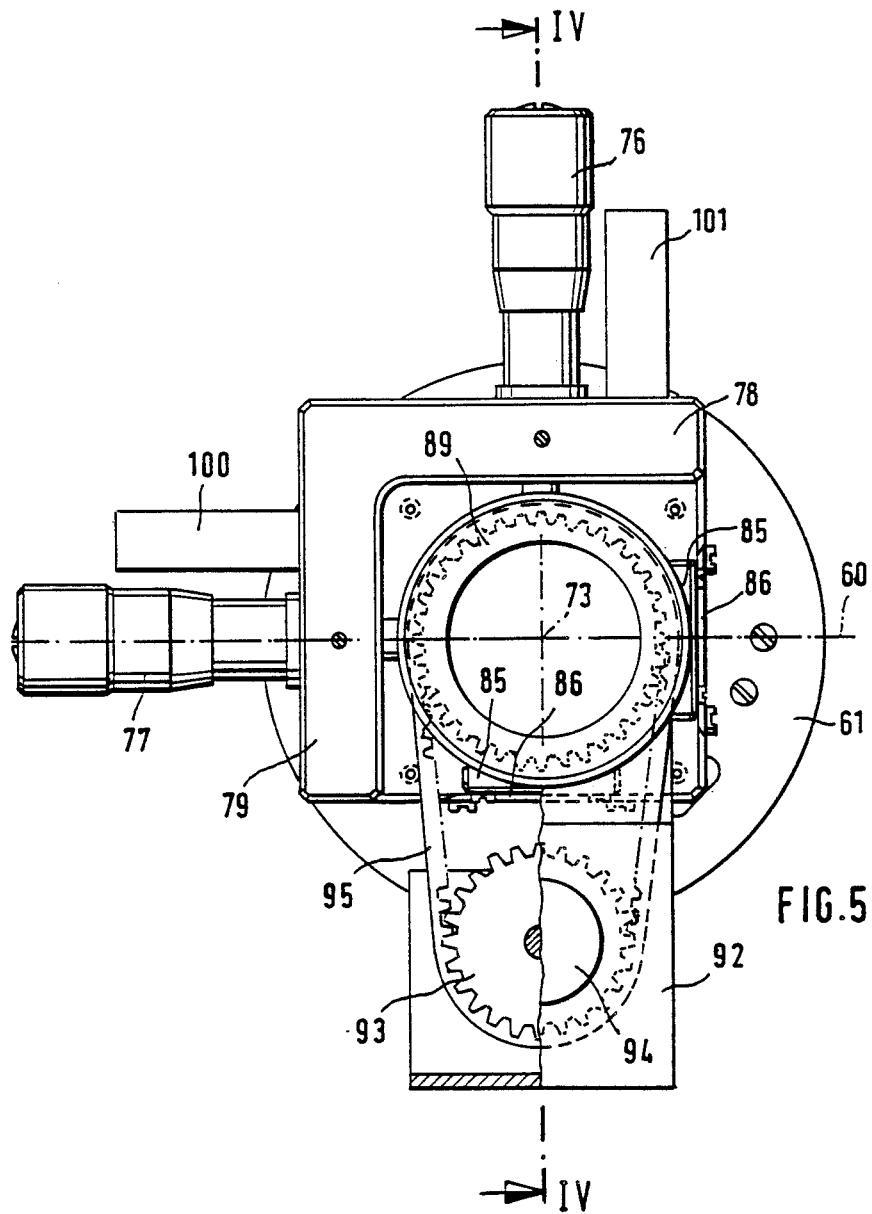
FIG. 5 shows a plan view of the holding means of FIG. 4.

The holding device 21 described above with reference to FIG. 2 is illustrated in a practical form of Embodiment in FIGS. 4 to 6. For the parts which have already been described above with reference to FIG. 2, the same reference numerals are used here. The outer housing 25 is mounted for pivoting about an axis 60 in the flange 61 which was mentioned above but not illustrated in FIG. 2. Secured to the outside of the outer housing 25 is a nut 62 in which a screw 63 is mounted for rotation, which screw rests with a rounded head 64 on the top 65 of the flange 61 and can be actuated via a handle 66. An extreme position of the outer housing 25 with the adjusting device 67 disposed thereon is illustrated in broken lines in FIG. 6.

The two-dimensional transverse movements along the arrows 32 and perpendicular thereto, the rotary movement according to the arrow 31 and the movement in the axial direction corresponding to the dfouble arrow 31 can be carried out with the adjusting device 67. The pivotal movement about the axis 60 is the movement corresponding to the double arrow 37 in FIG. 2.

The adjusting device 67 has a basic body 68 which is provided with a bore 69 corresponding to the internal diameter of the outer housing 25. A sliding surface 70 is provided transversely to the axis of the bore. The inner housing 28 is provided with a head portion 71 having a four-cornered surface area 72 which extends at an angle of 90° to the axis 73 of the inner housing 28. The inner housing 28 is mounted by the surface 72 on the sliding surface 70 for two-dimensional displacement. The head 71 of the inner housing 28 further comprises opposite inclined surfaces 74, 75 which are formed on the head 71 in pairs offset by 90° in each case. For the transverse adjustment, two adjusting screws 76, 77 are provided which are offset by 90° in relation to one another and may be constructed in the form of ordinary micrometer screws. These adjusting screws are disposed in the upright walls 78, 79 which extend upwards above the sliding surface of the basic body 68 and, as can be seen from FIG. 5, may form an angle.

As illustrated in FIG. 4, the micrometer screws are inserted with their housings 80 in bores 81 in the walls 78, 79. The threaded spindle 82 rests with a ball end 83 against the inclined surface 74 and is actuated vai a handle 84. Reduction gears may also be disposed between the threaded spindle and the handle.

Resting against the opposite inclined surface 75 is a cylindrical pin 85 which is secured to a leaf spring 86 and extends with its axis transversely to the inclined surface 75. This arrangement with the spring 76 and the pin 85 forms the counterforce whereby the inner housing 28 is held bearing against the ball end 83 of the threaded spindle 82. Finally, the head 71 is held with its sliding surface 72 bearing against the sliding surface 70 by the inclined surfaces 74, 75.

In the form of embodiment shown in FIGS. 4 and 5, an intermediate sleeve 87 is rotatably mounted in the inner housing 28. At its upper end, this intermediate sleeve carries a toothed ring 88 on which a rotary drive acts as will be described further below.

Mounted in the intermediate sleeve 87 is the tubular sample holder 26 which carries an actuating ring 89 at its upper end. The recess 27 to receive the sample 12 is provided at the lower end of the sample holder 26. The diaphragm 22 with its central sharp-edged aperture 22a is here secured to the lower end face 90 of the outer housing 25. Thus the diaphragm apeture 22a always lies concentrically round the point of incidence of the beam of light and does not move together with the sample as described above with reference to FIG. 2.

The transmitting apertures 34, 36 for the passage of the light beam component 1d penetrating through the sample are provided in the walls of the outer housing 25 and of the inner housing 28 respectively and are illustrated here offset through 90° in relation to the axis 60 for reasons of clarity of the drawing.

The inner housing 28 and the intermediate sleeve 87 are each provided with a plurality of elongated openings 91. In the form of embodiment illustrated, six such openings are provided, through which the beam of light can fall in six permanently preset rotary positions of the sample support. Provided between the intermediate sleeve 87 and the sample support 26 in this case are indexing means whereby assurance is provided that the openings in the inner housing 28 and in the intermediate sleeve 87 are each in alignment with one another. In the sample support 26, the openings 91 may be open through slits 92 to the end face of the sample support. In this manner, the lower end of the sample support is constructed with resilient tongues through which the sample is held in the recess 27 receiving it.

Secured to the top of the head 71 of the inner housing 26 is a holding means 93 which is here situated opposite the micrometer screw 76 and projects laterally beyond the basic body 68. Mounted for rotation in this holding means is a belt pulley 93 which is driven by a motor 94. By means of this belt pulley 93, which may again be constructed in the form of an externally toothed disc, the intermediate sleeve 87 and the sample holder mounted therein are rotatable via a toothed belt 95 which cooperates with the external toothed ring 88 of the intermediate sleeve 87. The particular angle of rotation can be read out through an angle indicator 96 which is driven by the belt pulley 93 from the motor 94. The motor 94 is constructed in the form of a stepping motor through which the sample holder 26 is driven into the rotational positions which are preset by the number of openings 91 in the sample holder 26 and in the intermediate sleeve 87.

The micrometer screws 76 may also be provided with stepping motors as drives. In order to determine the particular position, displacement pick-ups 100, 101 are provided which should be disposed parallel to the axis of the adjusting devices 76, 77 and likewise rest with a sensing element against the inclined surfaces of the head 71.

With the motorized drives and the displacement and angle pick-ups described, certain test programs for the samples can be preprogrammed and be carried out controlled by this program.

A change of samples can be carried out by simply pulling out the sample holder 26. The sample then only needs to be taken out of the recess 27 and a fresh sample inserted.

It will be understood that the above description of the present invention is susceptible to various modifications, changes and adaptations.

What is claimed is:

1. An apparatus for determining the effective surface roughness of a transparent optical sample, the surface of which is polished, by measuring the total scattered radiation therefrom, having an adjustable support for the sample, a source of laser light from which a beam of light is directed onto the surface of the sample at an angle between 15° and 45°, a light trap for the beam of light reflected from the surface of the sample, means for measuring the scattered light reflected from the surface of the sample, including a light detector and a display device for the measured scattered light, an aperture in the sample support for the beam emerging at the back of the transparent sample in the direction of the incident beam; a light trap disposed behind this aperture for this beam component, and a sample masking diaphragm disposed on the sample support having an aperture for the incident beam and for the beam reflected from the surface of the sample, said diaphragm is made light-absorbing in at least the region of the beam component reflected directly from the back of the transparent sample.

2. An apparatus according to claim 1, characterised by the use of the Ulbricht sphere which integrates the scattered light and which is coated on the inside thereof with an ideally scattering material and which is provided with a first aperture for the entry of the beam of light and a second apeture for the emergence of the beam reflected from the surface of the sample and with an adjustable support for holding the sample in the region of the sphere wall as well as comprising a detector disposed in the spere wall for the integral scattered light.

3. An apparatus according to claim 1, characterised by the use of the Coblentz hemisphere which is mirror-coated on the inside thereof and which is provided with a first aperture for the entry of the beam of light and a second aperture for the emergence of the beam reflected from the sample, wherein the point of incidence of light on the sample is offset laterally in relation to the axis of the hemisphere and the detector is disposed in the focal point of the scattered light of the sample reflected from the mirror-coated surface.

4. An apparatus according to claim 1, wherein the masking diaphragm is provided, in the region of the beam reflected from the back of the sample, with an aperture which is covered by a light trap.

5. An apparatus according to claim 4, wherein a polished silicon disc which is coated with at least one dielectric $\lambda/4$ layer, at least on the surface facing the aperture, is provided as a light trap for the radiation reflected at the back of the sample.

6. An apparatus according to claim 1, wherein the masking diaphragm is coated with at least one dielectric $\lambda/4$ layer, at least on the surface facing the surface of the sample.

7. An apparatus according to claim 5 or 6, wherein a $\lambda/4$ coating is provided consisting of a dielectric material having a refractive index $n \approx 2$.

8. An apparatus according to claim 7, wherein the coating consists of $Ta_2O_5$, $TiO_2$, $ZrO_2$ or $Al_2O_3$.

9. An apparatus according to claim 1, wherein the sample support is mounted with an outer housing in a flange which surrounds the aperture for the beam emerging at the back of the sample, and mounted in the outer housing is an inner housing with a sample holding means, which inner housing is adapted for adjustment inp the outer housing in two directions extending at right angles to the axis of the sample holding means and at right angles to one another, and the inner housing and the outer housing are provided with light transmitting apertures in the direction of the beam passing through the sample.

10. An apparatus according to claim 9, wherein the outer housing is pivotable, in the flange, about an axis which passes through the point at which the incident beam impinges on the surface of the sqample and which extends perpendicularly through the apex of the angle ($\theta$) between the incident and emergent beams.

11. An apparatus according to claim 9, wherein one of the adjustment directions of the inner housing in relation to the outer housing extends perpendicular to the pivotal axis and the other adjustment direction extends in the direction of the pivotal axis.

12. An apparatus according to claim 9, wherein the sample holder is mounted in the inner housing for rotation about the axis of the sample holder, said sample holder including a wall having a plurality of beam transmitting apertures therein.

* * * * *